United States Patent
Wang et al.

(10) Patent No.: US 9,816,823 B2
(45) Date of Patent: Nov. 14, 2017

(54) UPDATING ROAD MAPS

(71) Applicant: HEWLETT-PACKARD DEVELOPMENT COMPANY, L.P., Houston, TX (US)

(72) Inventors: Yin Wang, Sunnyvale, CA (US); George Forman, Port Orchard, WA (US); Xuemei Liu, Palo Alto, CA (US)

(73) Assignee: Hewlett Packard Enterprise Development LP, Houston, TX (US)

( * ) Notice: Subject to any disclaimer, the term of this patent is extended or adjusted under 35 U.S.C. 154(b) by 852 days.

(21) Appl. No.: 13/842,318

(22) Filed: Mar. 15, 2013

(65) Prior Publication Data
US 2014/0278055 A1    Sep. 18, 2014

(51) Int. Cl.
| G01C 21/32 | (2006.01) |
| G06F 19/10 | (2011.01) |
| G06F 17/30 | (2006.01) |
| G01C 21/36 | (2006.01) |

(52) U.S. Cl.
CPC ......... *G01C 21/32* (2013.01); *G01C 21/3617* (2013.01); *G06F 17/30* (2013.01); *G06F 19/10* (2013.01)

(58) Field of Classification Search
CPC ..... G01C 21/32; G01C 21/3617; G06F 19/10; G06F 17/30
See application file for complete search history.

(56) References Cited

U.S. PATENT DOCUMENTS

| 8,359,156 B2 | 1/2013 | Guo et al. | |
| 2003/0125871 A1* | 7/2003 | Cherveny et al. | ............ 701/208 |
| 2008/0262721 A1* | 10/2008 | Guo et al. | ...................... 701/208 |
| 2009/0125235 A1 | 5/2009 | Chen et al. | |
| 2009/0216704 A1* | 8/2009 | Zheng et al. | ................... 706/52 |

(Continued)

FOREIGN PATENT DOCUMENTS

| EP | 2541203 | | 1/2013 |
| WO | WO 2011047729 A1 | * | 4/2011 |

OTHER PUBLICATIONS

Cao and Krumm. "From GPS Traces to a Routable Road Map". ACM GIS '09. Nov. 4-6, 2009.*

(Continued)

*Primary Examiner* — Rami Khatib
*Assistant Examiner* — Jeffrey Boomer
(74) *Attorney, Agent, or Firm* — Fabian VanCott (57) ABSTRACT

A technique for updating road maps is disclosed. A number of GPS traces can be matched with a number of roads in a map. Matched GPS traces may be processed by a matched segment module to produce proposed changes to the map. The map can be updated using a map updating module based on the proposed changes from the matched segment module. Unmatched GPS traces may be processed by an unmatched segment module to produce proposed changes to the map. The map can be updated using a map updating module based on the proposed changes from the unmatched segment module. The proposed changes to the map may include metadata defining new roads in the map, new intersections in the map, updates to turn restrictions in the map, updates to the allowable directional traffic flow on the roads within the map, updates to road closures in the map.

18 Claims, 7 Drawing Sheets

(56) References Cited

U.S. PATENT DOCUMENTS

2010/0063727 A1* 3/2010 Umezu et al. ............... 701/208
2012/0277993 A1 11/2012 Mund

OTHER PUBLICATIONS

Bruntrup et al. "Incremental Map Generation with GPS Traces". Proceedings of the 8th International IEEE Conference on Intelligent Transportation Systems. Sep. 13-16, 2005.*
Schroedel et al. "Mining GPS Traces for Map Refinement". Data Mining and Knowledge Discovery. 2004.*
Zhang, L., et al. "Integration of GPS traces with road map." Proceedings of the Second International Workshop on Computational Transportation Science. ACM, 2010.

* cited by examiner

UPDATING ROAD MAPS

BACKGROUND

Global positioning satellites (GPS) systems allow a user to determine his or her position on the earth so long as the GPS system is in contact with a number of GPS satellites. GPS systems may also include a map which, when overlaid by the systems current position, may allow a user to navigate roads depicted on the map. In some GPS systems, the map may be out of date because, for example, new roads have been created, old roads have been destroyed, some roads are under construction, among other reasons. Additionally, data related to possible flow of traffic, possible turns at intersections, among others may simply be incorrect due to errors during the manual entering of the map data by a human.

BRIEF DESCRIPTION OF THE DRAWINGS

The accompanying drawings illustrate various examples of the principles described herein and are a part of the specification. The examples do not limit the scope of the claims.

Throughout the drawings, identical reference numbers designate similar, but not necessarily identical, elements.

DETAILED DESCRIPTION

Global positioning satellite systems are used by an increasing number of people for everyday tasks. These users across the globe rely on, for example, personal smartphones to help them navigate. The digital roads represented by these systems may, however, remain surprisingly inaccurate and incomplete. As a result, serious injuries have occurred from these users relying on the old and inaccurate information presented to them via the system.

Although road networks are frequently modified, those maps representing the road networks are not necessarily updated on a frequent basis. Indeed, for some GPS systems, the map data is only updated after customer support has altered specific data and delivered an update to the user. Most often this occurs when a user of the GPS system alerts those who maintain the map about the inaccurate or incomplete data. This type of system, therefore, relies on consumers of the system to take time to notify those responsible for updating the map about these issues. This may lead to user dissatisfaction as well as an ongoing inaccurate digital map.

Therefore, the present specification describes a system for updating road maps, comprising a processor; a database, comprising data describing a number of roads; a map matching module configured to match a number of GPS traces with a number of roads; a matched segment module configured to process GPS traces that are matched to a subset of the number of roads; an unmatched segment module configured to process GPS traces that are unmatched with a road among the number of roads; and a map updating module configured to update a number of roads based on proposed changes presented by matched segment module and the unmatched segment module.

The present specification further describes a method of updating a road map on a GPS device comprising, with a processor, matching a number of GPS traces to a number of roads within a map database with a map matching module, processing GPS traces that are matched to a subset of the number of roads with a matched segment module, processing GPS traces that are unmatched with the roads with an unmatched segment module, and providing, at a map updating module, a proposed change based on processed GPS traces received from the matched and unmatched segment modules.

Still further, the present specification describes a computer program product for updating road maps on a GPS device, the computer program product comprising a computer readable storage medium comprising computer usable program code embodied therewith, the computer usable program code comprising computer usable program code to, when executed by a processor, match a number of GPS traces to a number of roads within a digital map, computer usable program code to, when executed by a processor, process the number of GPS traces that are matched to a subset of the number of roads in the digital map, computer usable program code to, when executed by a processor, process the number of GPS traces that are unmatched to any road in the digital map, computer usable program code to, when executed by a processor, receive a proposed change to the digital map based on the matched and unmatched GPS traces, and computer usable program code to, when executed by a processor, provide a proposed change based on processed GPS traces received from the matched and unmatched segment modules.

In the present specification and in the appended claims, the term "road" is meant to be understood broadly as any digitally represented or real-world path by which a user of a GPS system may pass over. In some examples, the road may be represented either incorrectly or correctly in the digital map. In the real-world, the road may be a newly created path through which a vehicle, a cyclist, a pedestrian, etc. may travel in order to reach a destination.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language indicates that a particular feature, structure, or characteristic described in connection with that example is included as described, but may not be included in other examples.

Figure 1:
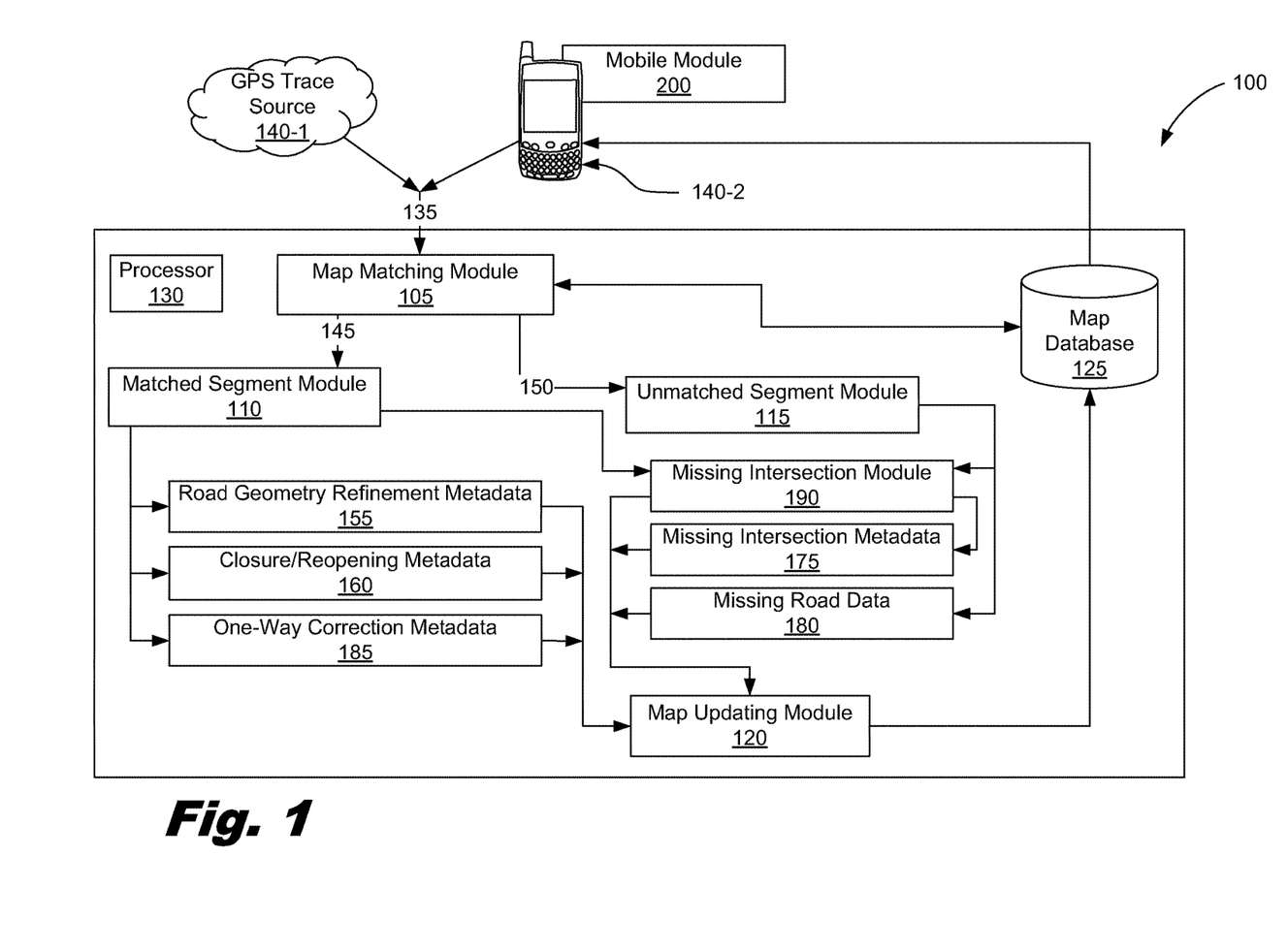
FIG. 1 is a block diagram of a system for updating road maps according to one example of principles described herein.

FIG. 1 is a block diagram of a system (100) for updating road maps according to one example of principles described herein. The system (100) comprises a map matching module (105), a matched segment module (110), an unmatched segment module (115), a map updating module (120), and a map database (125). Each of these modules (105, 110, 115, 120, 125) may be embodied as hardware, a combination of hardware and software, or a computer readable program code embodied on a computer readable medium which, when executed by a processor (130), performs the methods described below. Each of these modules will now be described in more detail.

In operation, the map matching module (105) receives a number of global positioning satellite (GPS) traces (135) from a number of GPS trace sources (140-1, 140-2). In the present specification and in the appended claims, the term "GPS trace" is meant to be understood broadly as any data defining the recent or past positions of a GPS system. Each GPS trace (135) comprises a sequence of GPS points comprising: latitude, longitude, and timestamp or time-delta. In one example, each GPS point may further comprise data describing the measured speed of the GPS system, the compass bearing at which the GPS system is directed towards, among others.

The GPS trace sources (140-1, 140-2) may comprise, for example, a GPS fleet management system implementing a GPS tracking system, live traffic traces delivered from a number of users' GPS systems, online navigation traces provided by a mobile computing device, among others. A number of different types of users may be carrying, for example, a GPS system or GPS-enabled computing device thereby also being potential GPS trace sources (140-1, 140-2). Therefore, the present disclosure contemplates a number and variety of sources from which the map matching module (105) receives GPS traces (135).

In one example, the map matching module (105) may receive a number of GPS traces (135) from a number of GPS trace sources (140-1, 140-2) in real-time by streaming the GPS traces (135) to the map matching module (105). In another example, the map matching module (105) may receive a packet of GPS traces (135) from each GPS trace source (140-1, 140-2) defining all GPS traces (135) within a period of time.

The system (100) further comprises a map database (125). The map database (125) may comprise an existing digital map of a geographical area. In one example, the digital map may be in a vector format. As described above, the digital map may initially include a number of inaccuracies or may be incomplete. During implementation of the system (100), the digital map stored in the map database (125) may be updated using the information processed by the map matching module (105), matched segment module (110), and unmatched segment module (115).

The map matching module (105), once it has received a number of GPS traces (135), processes those GPS traces (135) by matching them to a road defined in the digital map. The map matching module (105) matches each of the GPS traces (135) with the most likely road positions corresponding to a viable route through the digital map by using the processor (130) to execute a matching algorithm. In one example, the matching algorithm may be a Viterbi matching algorithm. Other algorithms may be used to match the GPS traces (135) to the roads defined in the digital map and the present disclosure contemplates the use of these alternative algorithms.

Where the GPS traces (135) do match a road defined in the digital map, the matched trace (145) to which the GPS traces (135) match is sent to the matched segment module (110) for further processing as will be described below. Where the GPS traces (135) do not match a road defined in the digital map, the unmatched trace (150) to which the GPS traces (135) are correlated with is sent to the unmatched segment module (110) for further processing as will also be described below.

The matched segment module (110) and unmatched segment module (115) both provide metadata (155-185) to the map updating module (120). The metadata (155-185) may include road geometry refinement metadata (155), road closure and reopening metadata (160), missing intersection metadata (175), missing road data (180) and one-way correction metadata (185). Each of these types of metadata will be described in more detail below.

The map updating module (120) then uses this information to update the digital map in the map database (125). In one example, the system (100) may notify a user that the map updating module (120) has metadata (155-185) to update the digital map with and request from the user authorization to do so. In this example, a user may confirm visually that the current digital map is incorrect and is to be updated based on the proposed change.

In one example, the newly updated map database (125) may provide the new updates to the GPS trace sources (140-1, 140-2), the map matching module (105), and other digital map providers interested in digital map data or updates on digital maps. The GPS trace sources (140-1, 140-2) may use the map database (125) as a source of digital map in order to navigate a number of roads. The map matching module (105) may use the newly updated map database (125) to further refine the digital map using the system (100) described above.

The processor (130) provides processing power to the map matching module (105), matched segment module (110), unmatched segment module (115), and map database (125) to complete the generation of the metadata (155-185) and update the digital map on the map database (125).

In one example, after the system (100) has updated the digital map on the map database (125), portions of the digital map may be sent to some GPS trace sources (140-1, 140-2) for individual use to the updated digital map. In this example, a mobile module (200) may be included on the GPS trace sources (140-1, 140-2).

Figure 2:
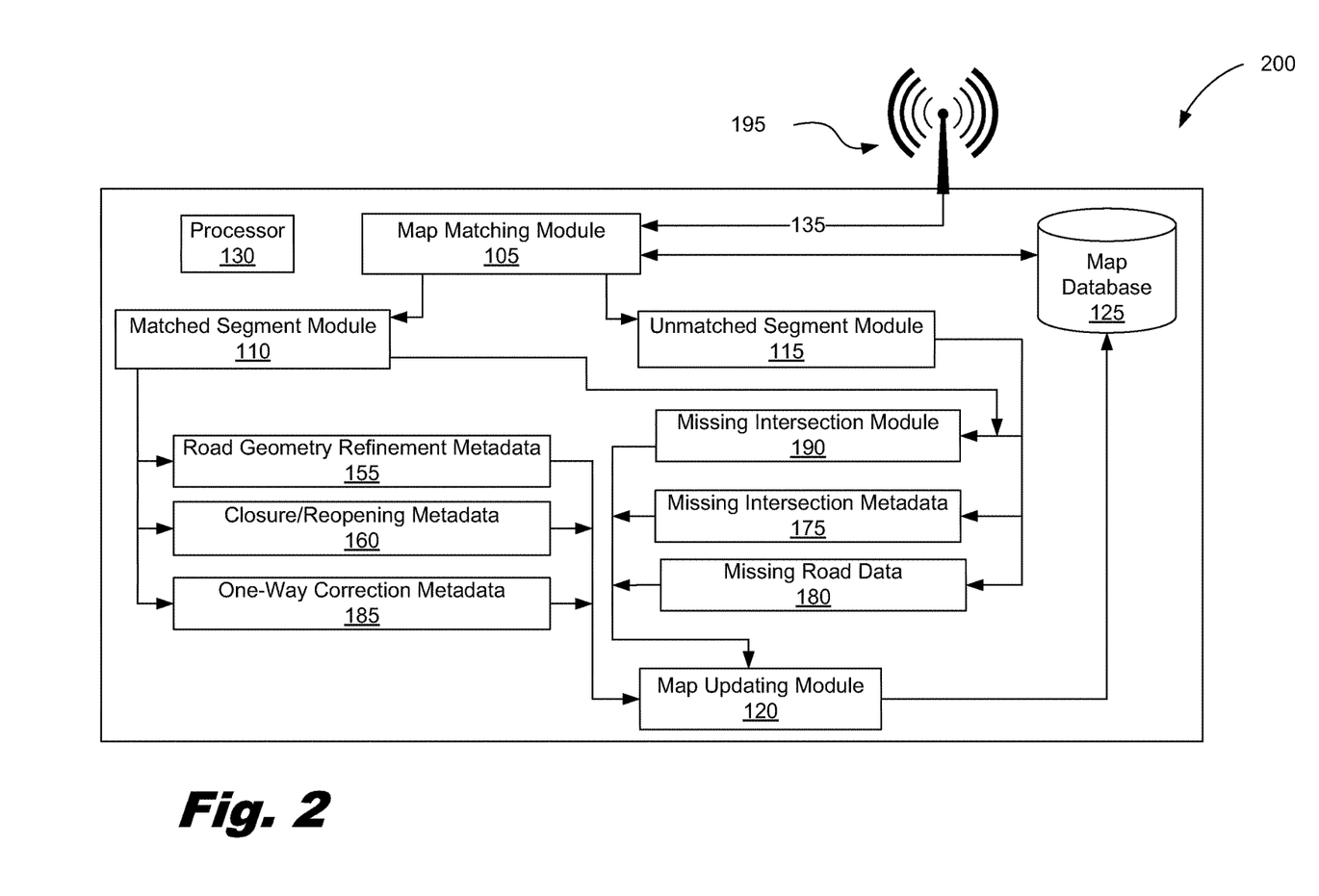
FIG. 2 is a block diagram of a mobile module for updating road maps according to another example of principles described herein.

Turning now to FIG. 2, a block diagram of a mobile module (200) for updating road maps is shown according to another example of principles described herein. The mobile module (200) may comprise a matched segment module (110), unmatched segment module (115), map updating module (120), map database (125), and processor (130) similar to that described in connection with FIG. 1. The mobile module (200) may further comprise an antenna (190) which may send digital map data or receive digital map data at a computing device on which the mobile module (200) is running. In one example, the mobile module (200) may allow a user of the device on which it is running to upload newly updated digital map data from a map database (FIG. 1, 125) in order to update its own map database (125). In this example, the mobile module may store its own updated digital map data as well as download new updates to the digital map from other mobile modules (200) or the system (100) described above. The mobile module (200) may also receive a number of GPS traces (135) from other GPS trace sources (140-1, 140-2) and update its own digital map using the process similar to that described in connection with FIG. 1.

Figure 3:
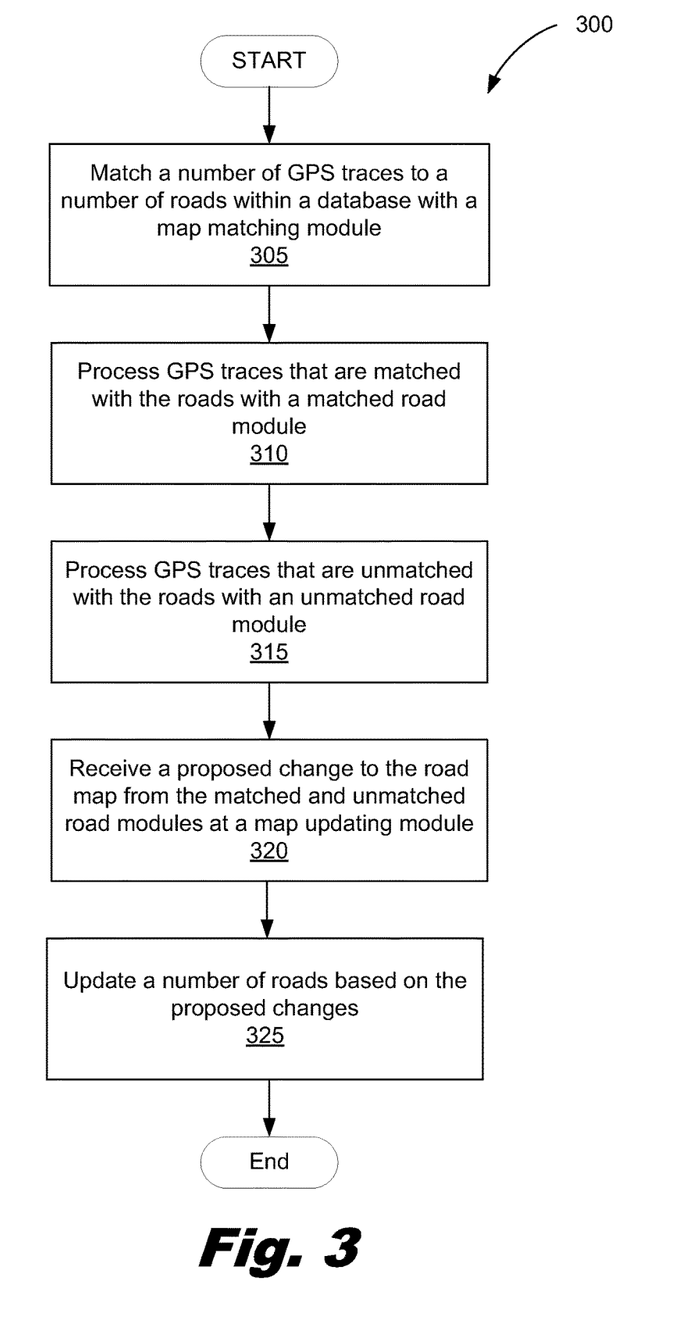
FIG. 3 is a flowchart describing a method of updating a road map on a GPS device according to one example of principles described herein.

Turning now to FIG. 3 and with reference to FIGS. 1 and 2, a flowchart describing a method (300) of updating a road map on a GPS device is shown according to one example of principles described herein. The method (300) may begin with matching (305) a number of GPS traces (135) to a number of roads within a map database (125) with a map matching module (105). As described above the GPS traces (135) may be received from a number of GPS trace sources (140-1, 140-2).

The method (300) may continue with the matched segment module (110) processing (310) the GPS traces (135) that are matched with roads at the map matching module (105). In this case, certain metadata may be created using this matched trace data such as the road geometry refinement metadata (155) and road closure and reopening metadata (160) briefly mentioned above. Additionally, the matched segment module (110), along with the unmatched segment module (115) may further help to create the missing intersection metadata (175) also briefly mentioned above.

The method may also comprise processing (315) GPS traces (135) that are unmatched with the roads with an unmatched segment module (115). In this case, certain metadata may be created using this unmatched trace data such as the missing road data (180) and one-way correction metadata (185) briefly mentioned above.

A proposed change to the digital map may then be received (320) at the map updating module (120). The processor (130) may then cause a number of roads in the map database (125) to be updated (325) based on the proposed changes.

The method (300) described above may also include sending a notice to the user of the system (100) or mobile module (200) before updating the number of roads based on the proposed changes presented by the unmatched segment module (115) and matched segment module (110). This additional process may allow the user to determine visually if the update to the digital map is appropriate and confirm that it is. This advantageously provides the system (100) with a number of individuals who can verify the update data is correct. This results in operators of the system not having to hire any or additional employees to update maps manually saving costs as well as lag in updating digital maps.

In one example, the mobile module (200) may be made to be map-inaccuracy aware by employing a dynamic sampling rate. The dynamic sampling rate may increase the sampling rate when the mobile module (200) detects that there are inaccuracies in the digital map using its map matching module (FIG. 2, 105). If a route the user is recognized to be traveling on the digital map on the computing device running the mobile module (200), the sampling rate may be lowered. This feature allows a user to save data bandwidth and wireless communication costs during periods where the metadata defining the digital map is sufficient enough to navigate while allowing refinement of a road in the digital map to be updated with relatively finer accuracy along roads that are inaccurate in the map database (125).

In another example, a dynamic error radius may be employed by the mobile module (200). Here different radii may be selected to match the GPS traces (135) to a road in the digital map. This allows the mobile module (200) and system (100) to tradeoff dynamically between precision and recall. For example, a large radius can match noisy traces to existing roads but may miss close parallel roads. Dynamically, the radius may be switched to a relatively smaller radius thereby producing numerous unmatched segments due to noise. As a result, if the user of the GPS system is traveling on a new road closely parallel an existing road, the new road can be detected as long as the value returned by the GPS trace source (140-1, 140-2) or mobile module (200) is less than half of the distance between the new road and the existing parallel road. On the other hand, if the GPS traces (135) are noisy, the value returned by the GPS trace sources (140-1, 140-2) or mobile module (200) is high and the GPS traces (135) are either matched to an existing road due to the large radii associated with its samples, or discarded if the accuracy is above a threshold.

In yet another example, each GPS trace (135) may be processed by the map matching module (105) independently and in parallel allowing for multithreading or distributed computing. In another example, the mobile module (200) may perform its own GPS map matching using its own map matching module (105) and send only the unmatched portions to the system (100) for clustering. One advantage of sending only the unmatched portions to the system (100) is that it reduces communication costs, and offloads the map matching effort from the system (100) for improved scalability. Additionally, in other examples, during parallel map matching or other map update tasks, data may be partitioned by a spatial grid or using political boundaries. Therefore each thread or node handles only a fixed area of data and can cache the relevant digital map for more efficient operation.

In one example, the GPS trace sources (140-1, 140-2) may be capable of presenting to the system (100) a detailed description of the type of vehicle within which the GPS system is operating. As a result, some GPS traces (135) originating from some types of GPS trace sources (140-1, 140-2) (e.g., farm equipment) may be ignored by the system (100) because a relative majority of the time these vehicles are not traveling or will not travel on real-world roads. In some examples, however, GPS traces (135) from other types of GPS trace sources (140-1, 140-2) (e.g., ATVs) may be used to create or update certain trails in, for example, a national forest.

In other examples, the type of vehicle associated with the GPS system may provide additional route information to the specific type of vehicle. The system (100) or mobile module (200) may track what type of vehicles frequently travel specific roads in the digital map. For example, a road that no truckers ever take will be marked as such. This is done so that when a truck driver uses a road so marked, they will get a notice that caution is advised because it is a route not normally traveled by a trucker. This may be because of specific hazards special to the size of the truck. The metadata created by the system (100) and mobile module (200) may also be used by a trucker to plan a route most traveled by truckers and therefore strongly prefer those roads that are typically used by other truckers. This type of process may also be run for other specialized populations; e.g. skiers on backcountry trails, hikers on wilderness trails, etc.

Still further, in some examples spatial indexing may be used in the system (100) and mobile module (200) for more efficient computation. All spatial databases support spatial indexing, and the present system (100) and mobile module (200) may use this feature to quickly locate the relevant map data for each GPS trace (135). The map matching module (105) caches the digital map in memory and builds an in-memory spatial index to quickly find the set of roads near a sample. In another example, the unmatched segment module (115) has its own in-memory spatial index associated with it to index the GPS traces (135) and speed clustering as will be described below.

In addition to caching the digital maps in memory for more efficient computation, in one example, a version number may be assigned to each road to detect possibly outdated unmatched roads, and the system (100) or mobile module (200) may rematch received GPS traces (135) using the latest updated digital map. When, for example, a new road is inserted into the digital map, the version numbers of its anchor roads on both ends are incremented. An unmatched segment may be re-matched if at least one of its anchor roads is not current.

In the system (100) as well as the mobile module (200) the map matching module (105), matched segment module (110), and unmatched segment module (115) may work together to generate the metadata (155-185) as briefly described earlier. The processes by which the system (100) and mobile module (200) generate each of these types of metadata will now be described.

Missing Road Data

Figure 4:
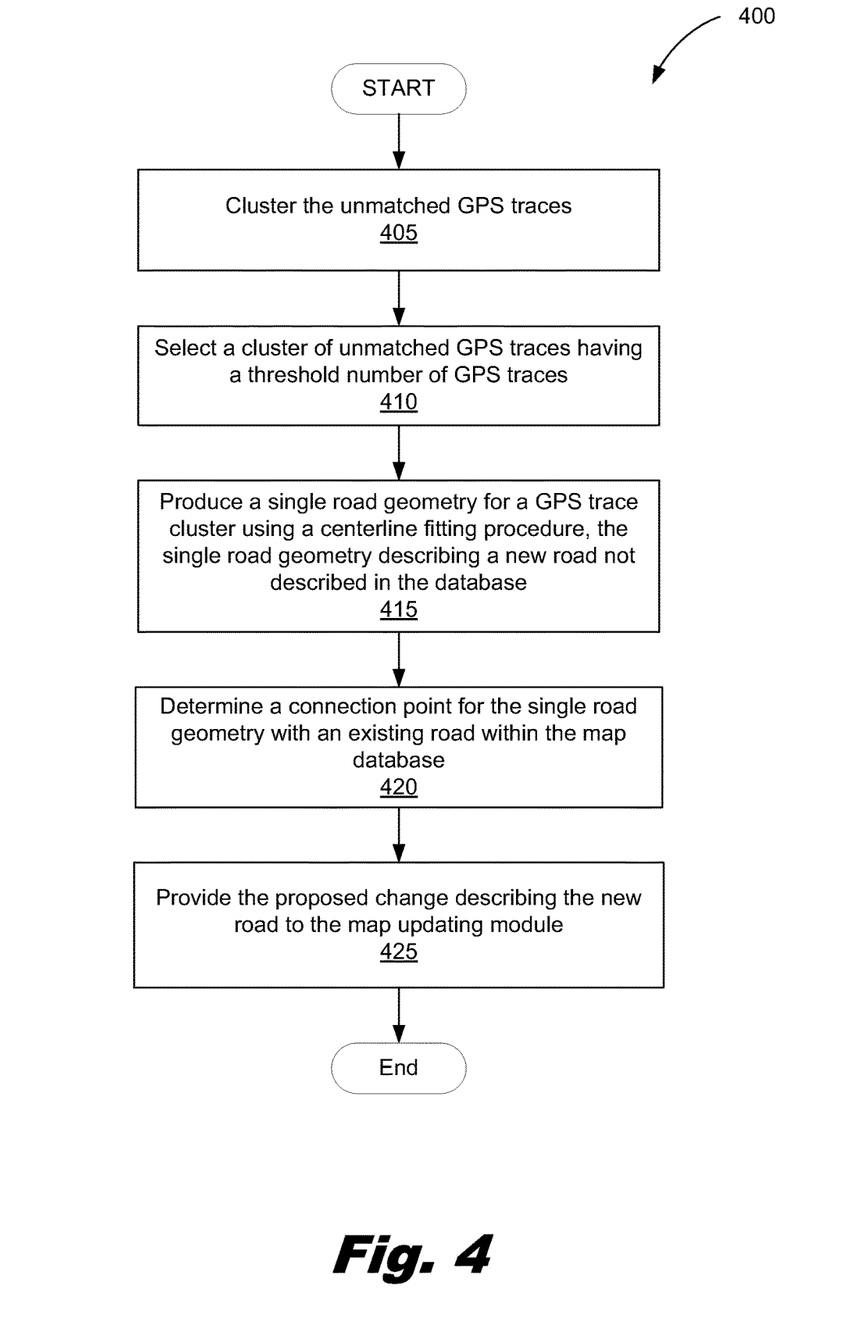
FIG. 4 is a flowchart describing a method of updating a digital map with missing road metadata according to one example of principles described herein.

Turning now to FIG. 4 and in reference to FIGS. 1 and 2, a flowchart describing a method (400) of updating a digital map with missing road data (180) is shown according to one example of principles described herein. The method (400) may begin with the unmatched segment module (115) clustering (405) the unmatched GPS traces (135) received from the map matching module (105). Many available algorithms may be suitable for this process, but in one example, an agglomerative clustering algorithm that iteratively compares GPS traces (135) with each other and combines those that fall within a pre-determined tolerance into a cluster may be used, One example of such an algorithm uses the Hausdorff distance as its distance measure in the clustering algorithm.

The method (400) may continue by selecting (410) a cluster of unmatched GPS traces (135) having at least a threshold number of GPS traces (135). In one example, where a cluster of GPS traces (135) comprises less than a total of 5 GPS traces (135) the cluster is not selected (410). However, where the cluster does comprise 5 or more GPS traces (135), the cluster may be selected (410) and used in the method.

Once the cluster is selected (410), the unmatched segment module (115) may produce (415) a single road geometry for a cluster of unmatched GPS traces (135) using a centerline fitting procedure in which the single road geometry describes a new road not described in the map database (125). In one example, a polygonal principal curve algorithm or a Trace Clustering Algorithm (TC1) algorithm as described in "Mining Large-Scale, Sparse GPS Traces for Map Inference: Comparison of Approaches" by X. Liu; J. Biagioni; J. Eriksson; Y. Wang; G. Forman; Y. Zhu. (http://www.hpl.hp.com/techreports/2012/HPL-2012-134.html) may be implemented by the processor (130). The above reference is herein incorporated by reference.

The method (400) may continue with the unmatched segment module (115) determining (420) a connection point for the single road geometry with an existing road within the map database (125). A number of different algorithms executed by the processor (130) may be used to make this determination. In one example, a set of matched points before and after each unmatched segment in each unmatched GPS trace (135) is considered before determining the estimated road position of the road that is the closest. In another example, the point on a connecting road that intersects the ray of the new road's end segment is considered. In yet another example, an existing intersection node on an intersection connecting road is considered. In this example, the system (100) and mobile module (200) avoids producing needless intersection points next to already existing intersection points defined in the digital map.

The method may end with providing the proposed change describing the new road to the map updating module (120). Here the digital map is modified to include the new road, including possibly new intersections in the base map and any associated pointers or indices updated.

In one example, a notice may be displayed to a user of the GPS system (100) or mobile module (200) before updating (425) the map database with the metadata (180) defining the new road. Giving such a notice to users of the GPS system (100) or mobile module (200) presents a user of the GPS system with the opportunity to reject any proposed update to the digital map in the map database (125). In the standalone mode example, a user may simply look to determine if the new road does exist in the real-world and accept the change to the digital map if correct.

In some examples, once a road is updated in the digital map, the nearby GPS traces (135) can be re-processed through the map matching module (105) described above in connection with FIGS. 1-3. Some of the GPS traces (135) received by the map matching module (105) may then be determined to match the new road. In some cases, there may be no unmatched roads nearby while, in other cases, shorter unmatched roads may be present for other missing roads. By running the method described above in connection with FIG. 4 iteratively, the system (100) of mobile module (200) can acquire additional roads while existing roads may be leveraged to help split up the GPS traces (135) into clusters of GPS traces (135) that comprise the above mentioned threshold limit of GPS traces (135).

As briefly mentioned above, the system (100) can also be used in a standalone mode by a single portable GPS-enabled device, such as a smartphone miming the mobile module (200). In this example, when trying to map out a missing road, the processed algorithm as described may wait until the threshold number of GPS traces (135) have been received by the GPS-enabled device before running the algorithm or a single GPS trace (135) may be used to define the new road. Consequently, in this example, the method described above can eliminate the process of selecting a cluster of unmatched GPS traces that only have a threshold number of GPS traces and/or the process of clustering the unmatched GPS traces altogether. This allows an individual to pass over a new road once and have it immediately proposed as a change to the digital map.

In another example, the system (100) and mobile module (200) can also be used for refining the geometry of an existing road. In this example, given a selected, existing road in the map such as a road that shows consistently high error or sideways bias in the road matching, the system (100) and mobile module (200) may use all of its matching GPS traces (135) as a single cluster and run the final processes of the algorithm starting with centerline fitting. Alternately, the existing road defined in the digital map may first be removed from the digital map and a new road fitted.

Missing Intersection Metadata

Figure 5:
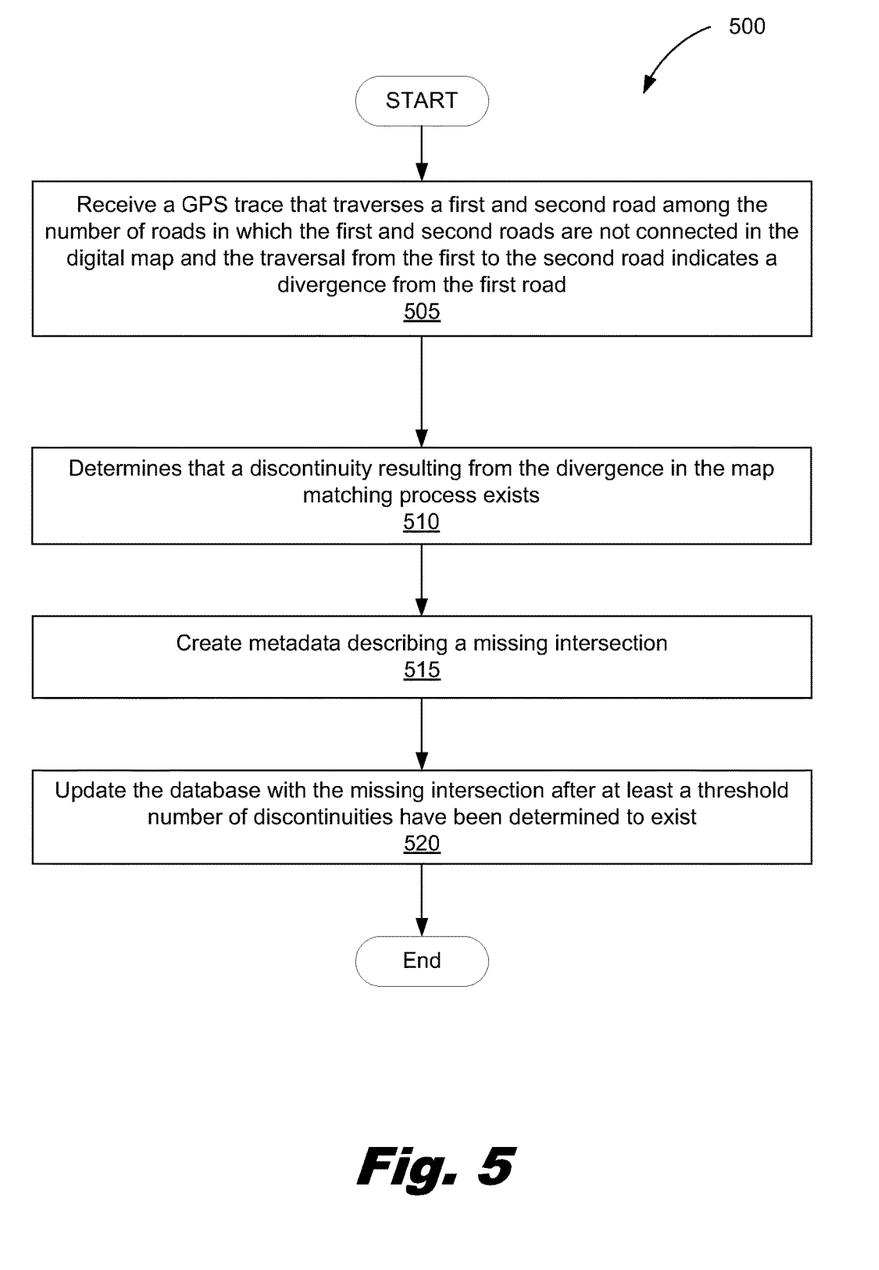
FIG. 5 is a flowchart describing a method of updating a digital map with missing intersection metadata according to one example of principles described herein.

FIG. 5 is a flowchart describing a method (500) of updating a digital map with missing intersection metadata according to one example of principles described herein. The method (500) may begin with the map matching module (105) receiving (505) a GPS trace (135) that traverses a pair of roads, for example, a first and second road among the number of roads, that are not connected in the digital map being matched to. The map matching module (105), after having matched the first road of the pair, will find increasing divergence from the first road for the subsequent GPS points that are actually on the second road which has no connection in the digital map for the map matching module (105) to follow. When this divergence exceeds a distance threshold, the map matching module (105) will note the resulting discontinuity and recover by matching the subsequent GPS point to the second road by considering the proximity of the GPS point to the second road, without regard to the lack of connectivity from the first road to the second road in the map. This indicates to the system (100) that there may be a discontinuity in the GPS traces (135) due to a missing intersection.

The method (500) may continue with the map matching module (105) determining (310) that a discontinuity in the map matching process exists based on whether a first OPS point in the GPS trace (135) after the discontinuity is n matched with the second road is within a threshold distance from the previous point matched from the GPS trace (135), whether the subsequent GPS points of the GPS trace (135) continue to match with the second road, and whether the first mad and the second road overlap geometrically in the map database (125) or come near each other within a radius around the discontinuity. When these conditions hold, the discontinuity between where the GPS system (100) first determined what mad the user was on and where the GPS system eventually acquired a new road indicates to the GPS system that the first road and the new road should be connected by a missing intersection.

When the map matching module (105) determines that the discontinuity exists, the matched segment module (110) and unmatched segment module (115) send the matched traces (145) and unmatched traces (150) onto a missing intersection module (190) which creates (515) metadata describing the missing intersection. In one example, a request for metadata describing the new intersection between the two roads can be flagged for manual editing. In another example, the geometry of the missing intersection can be estimated by the GPS system (100) or mobile module (200). For example, if the geometries of the first and second roads intersect within a distance threshold (e.g., 20 m) of the map matching discontinuities, then the point of intersection between the two roads is marked as the intersection. If the two roads merely come close but do not actually overlap in the region, then the point of connection for each road is the closest point to the other road in the region. If the two connection points are greater than a distance threshold (e.g., 50 m), then this connection can be discarded completely or else marked as "suspicious" requiring editorial approval before insertion into the digital map. The map updating module (120) may then update (520) the database with the missing intersection after a threshold number of discontinuities have been determined to exist.

In one example, evidence may be accumulated from multiple traces for the existence of an intersection at any location between the two roads. When enough data has accumulated (e.g. 5 such traces), a decision is made that the intersection is truly missing. Alternatively, without accumulating a number of GPS traces (135), a single GPS trace (135) may be deemed sufficient evidence. In some situations, this may risk that GPS noise may induce some errors. However, this may be acceptable especially where an editor or user of the GPS system reviews the changes before the changes are used to update the digital map.

For digital maps that include turn restrictions (e.g., a "no left turn" designation on a digital road going into an intersection), the system (100) or mobile module (200) may further determine which restrictions are not in effect for actual real-world traffic. In this case, the map matching module (105) obeys such turn restrictions. After the road has been picked up again after a discontinuity of the GPS trace (135) beyond the distance threshold, a check is made to determine whether there is an existing intersection for which a turn restriction was the cause of the map matching discontinuity. If so, this trace is treated as evidence that the turn restriction may not exist in the real-world. After a threshold number of GPS traces (135) have indicated that the turn is actually being made, the map updating module (120) may update the metadata defining this turn in the map database (125). Additionally, because some drivers will choose to violate turn restrictions, the threshold would be set to account for such behavior. In some cases one may set a higher threshold for relaxing turn restrictions than for adding missing intersections, or require a certain rate of accumulation (e.g. more than 50 turns per day) in order to allow the system (100) and mobile module (200) to update the digital map to reflect the new turn or erroneous turn metadata.

Even still, some turn restrictions are dependent on the time of day. These time dependent turns allow for better flow of traffic at different times of day so as to better manage commuter time for example. Similar to above, GPS traces (135) may be acquired and the process described in connection with FIG. 5 may be separately repeated throughout the day for a number of different time intervals. By doing so, any time variable turn restrictions may be identified or updated and the metadata describing these restrictions may also be added to the digital map.

One-Way Correction Metadata

Figure 6:
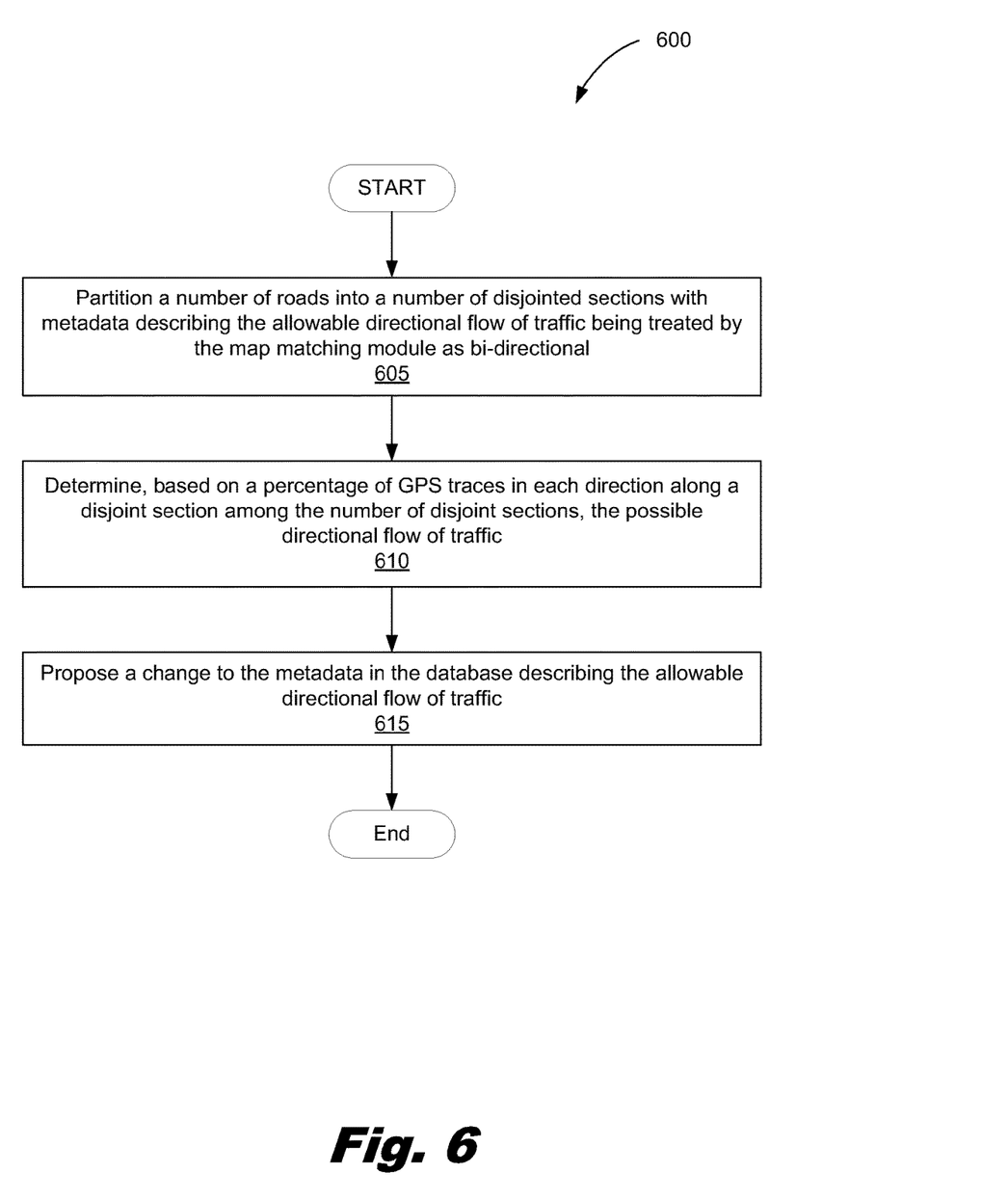
FIG. 6 is a flowchart describing a method of updating a digital map with one-way correction metadata according to one example of principles described herein.

FIG. 6 is a flowchart describing a method (600) of updating a digital map with one-way correction metadata (185) according to one example of principles described herein. The method (600) may begin with partitioning (605) the number of roads in the digital map into a number of disjointed sections with metadata describing the allowable directional flow of traffic being treated by the map matching module (105) as bi-directional. In the context of one-way correction metadata, the term road is meant to be understood as meaning road segments with each road segment being partitioned (605) into a number of disjointed sections defined by a portion of the road that begins and ends with an intersection.

After partitioning (605), the map matching module (105) determines (610), based on a percentage of GPS traces in each direction along a disjoint section among the number of disjoint sections, the possible directional flow of traffic. Here, as GPS traces (135) are provided to the map matching module (105), those traces that match a section are associated with the section. As the section accumulates a number of GPS traces (135), the matched segment module (110) looks at the proportion of GPS traces (135) indicating traffic flow in each direction along the section.

If a threshold proportion of GPS traces (135) indicate that traffic is to flow in a certain direction, the matched segment module (110) may compare this to the metadata associated with the digital map. If the metadata indicates that the permissible flow of traffic is contrary to the determined permissible traffic flow direction, then the matched segment module (110) may propose (615) a change to the metadata in the map database (125) describing the allowable directional flow of traffic. In one example, marking the section as bi-directional will not occur unless 98% or more of the traffic goes in only one direction. In other examples, various thresholds may be set to determine (610) the possible flow of traffic.

In one example, once a decision had been made with regard to the possible flow of traffic for any given section and the decision is inconsistent with the metadata in the map, the system (100) may automatically update the map accordingly. In another example, the system (100) may send a notice to a user of the GPS system requesting confirmation that the metadata should be changed.

In another example, the mobile module (200) may send into the system (100) only unmatched segments of GPS traces (135). This may reduce the communication costs as well as the processing load on the system (100). Pre-filtering the GPS traces (135) to include only those that do not match the digital map may be done before the map matching module (105) receives the GPS traces (135).

In a further example, the map matching algorithm not only outputs the location each GPS point of the GPS trace (135) matches to, but also gives the path (e.g., shortest-distance, or shortest-time path) between two consecutive matched GPS points. All road sections along these paths are considered being matched, and the GPS traces (135) are matched to them. Consequently, long-sampling-interval data may also be leveraged.

In yet a further example, multiple roads can be joined into a common section where their intersection allows no other path for traffic, for example, where exactly two roads terminate at an intersection. In this case, by treating the number of sections as one decision, there may be a greater chance of getting sufficient GPS trace (135) matches data to make a decision. If kept separate, each section may have to wait longer for sufficient GPS traces (135) to be associated with them, which may increase the time to decide the possible directional traffic flow for short residential streets that are rarely traversed by vehicles.

Additionally, sections may be merged together into a single section to obtain sufficient data sooner for making a decision on the one-way properties of the combined section. In some cases, partitioning (605) the road into sections may result in relatively short sections. In this example, a pre-determined threshold for the minimum section length may be established in which, if the section does not meet the minimum section length, it may be merged with another neighboring section, skipping intersections that occur before the minimum length has been met. Alternatively, where the metadata associated with the digital map has some indication of which roads are more traveled than others, a road can be partitioned (605) in by the more traveled roads first, working down in priority order to the less traveled roads. Once a road section is shorter than minimum length threshold, it will not be further partitioned.

In still another example, when a decision is reached (610) for a section of road, the system (100) may deduce the implied one-way constraints of intersecting road sections. Every intersection may have at least one source road to provide cars and at least one sink road to take them away. Consequently, when a road is freshly decided to be one-way, if it leads away from an intersection and there is only a single undecided road that could provide a source of cars to the intersection, then the system can conclude that it must at least be a source. Likewise, if it leads toward an intersection and there is only a single undecided road that could remove the cars, then the system (100) can deduce that the undecided road must not be one-way toward the intersection. Reaching these implied conclusions may lead to more decisions being made sooner, without waiting for more data for each section.

Closure/Reopening Metadata

Figure 7:
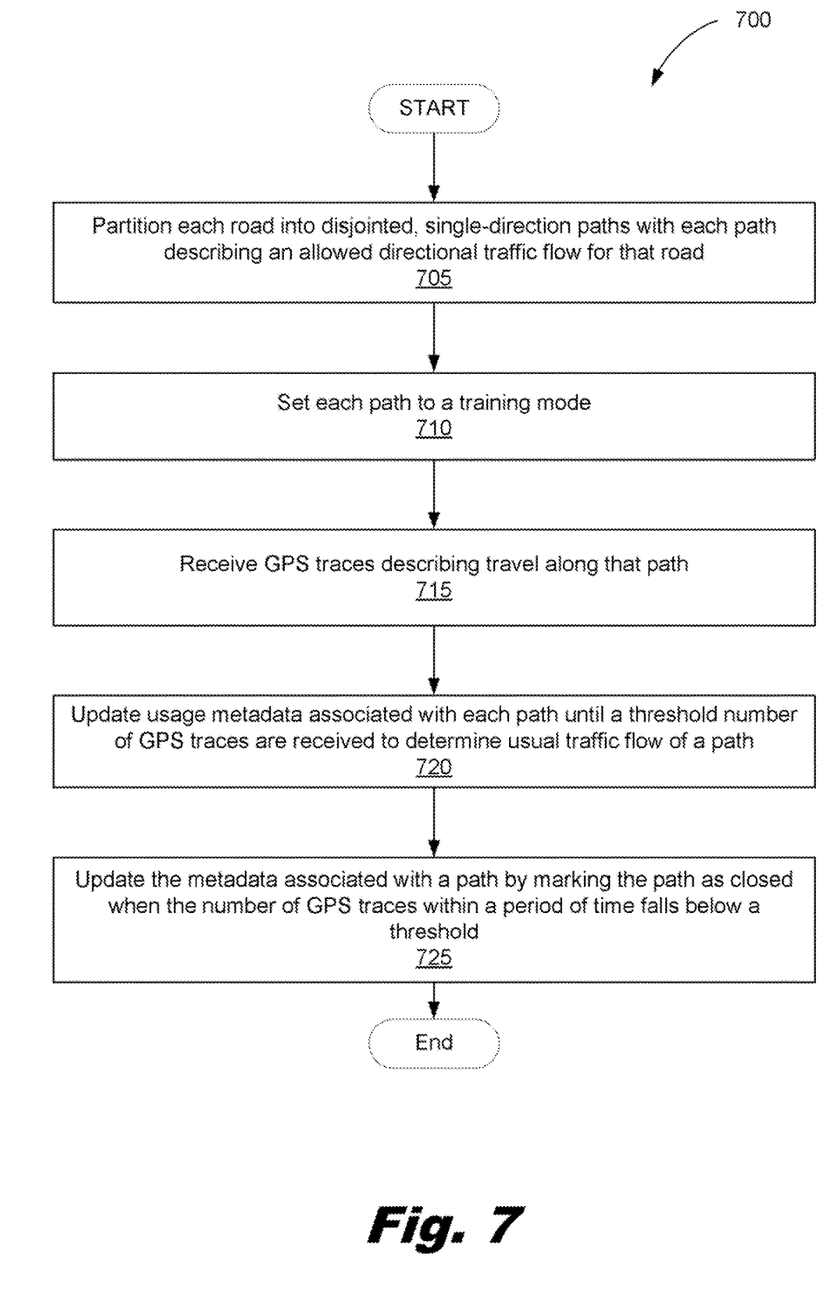
FIG. 7 is a flowchart describing a method of updating a digital map with road closure metadata according to one example of principles described herein.

FIG. 7 is a flowchart describing a method (700) of updating a digital map with road closure metadata according to one example of principles described herein. The method (700) may begin with the map matching module (105) partitioning (705) each road into disjointed, single-direction paths with each path describing an allowed directional traffic flow for that road. In one example, the beginning and ending of each path may be defined by neighboring intersections on the map.

The map matching module (105) may then set (710) each path to a training mode and receive (715) GPS traces describing travel along that path. If GPS traces (135) are, for example, 30 seconds apart, there may be some short paths that are inferred to have been traveled but which do not actually have an associated GPS points provided to the map matching module (105). If, however, there is a gap in samples of, for example, 5 minutes, then the system (100) considers this a gap in the GPS trace (135)

The map matching module (105) may then update usage metadata associated with each path until at least a threshold number of GPS traces (135) are received to determine usual traffic flow of a path. In one example, a counter may be incremented so as to determine when at least a threshold number of GPS traces are received to determine usual traffic flow of any path. In another example, the system (100) may increment a histogram counter per hour-of-day, or hour-of-week. In yet another example, the system (100) updates a stored timestamp of the most recent traversal and some statistics about the time since the previous traversal, such as tracking the maximum time difference. In another example, the system (100) updates a time-decayed exponential traffic flow average and tracks its minimum. In still another example, the system (100) inserts the timestamp into a list for later analysis, for example, if the data does not arrive in order.

The threshold number of GPS traces (135) received before proceeding through the method may vary. In one example, the system (100) waits until at least 1000 GPS traces (135) have been collected for the path and at least one week of data has been processed. Various thresholds may be used; a higher threshold will leave many rarely driven roads in the "still training" mode longer. A lower threshold will yield more paths that are done training, but with less data and therefore more variance in their models. In one example, it is a synchronous decision for all paths to be done training after, for example, 1 month of GPS traces (135) are processed.

Once enough data has been gathered for a path, the path may be marked as "trained" and is ready to detect closures. Some computation may be performed to distill the tracked statistics into a model. In some examples, the model represents the average, minimum, or, for example, 5th-percentile of traffic flow. In another example, the computation may be computed separately for each hour of the day, or each hour of the week, etc.

If a path has been declared to be trained, then traffic flow is tracked across the path by receiving map matched segments of GPS traces (135). A time-out may be attempted to be established in which the timeout is based on the information in the model. In one example, the time-out represents the time it would take to witness, for example, 100 vehicles under historically low traffic conditions. In some examples, there may have been so little traffic during training period of the path that the timeout may be set for decades into the future. These paths may be processed as described above or else the individual paths' processing may be deactivated to reduce overhead.

If the time-out expires with traffic tallied then the time-out is reset. In alternate examples, each time there is fresh traffic, the time-out is reset. If the time-out expires without traffic, then the path is marked as "closed," and its traffic counter is set to zero. The metadata describing this situation is updated (720) to the map database marked as unusable for navigation presently, and/or flagged on a map for user benefit or editor review.

If the path is marked as "closed," then its traffic counter is incremented. Once the path has accumulated, for example, 5 new GPS traces (135) within some time period (e.g., an hour or a day), then it is marked as reopened, this information is propagated to the map database with the path's state being returned to "trained" in order to watch for future closures.

In one example, it may be assumed that there were no actual closures during a training period. If there were closures, they may be manually tracked and prevented from affecting the traffic model for those paths affected. If these paths are not prevented from affecting the traffic model, these particular paths will be more insensitive to a lack of GPS traffic.

In some examples, after several months of GPS trace (135) data for a large number of vehicles has been processed, the system (100) may flag any paths that still have not received traffic as being "suspect." This may indicate that these roads in the map that are actually non-existent. The use of this flag may vary. In some examples, such flagged roads are avoided by the GPS navigation system when planning routes. In other examples, such roads can be included but appropriate warnings may be issued to a user of the GPS navigation system. In some examples, such flagged "roads" without traffic are brought to an editor's or user's attention, displayed along with an aerial image of the region.

Large scale GPS traces (135) may have long sampling intervals to reduce the communication and storage cost. Under a long sampling interval, two consecutive samples may cross multiple road segments and street blocks. In one example, the map matching algorithm not only outputs the location each sample matches to, but also gives the path (e.g., shortest-distance, or shortest-time path) between two consecutive matched locations. All road paths along these segments are considered being matched and the trace is added to their traffic statistics. The present system (100) may also, therefore, leverage long-sampling-interval data in order to determine whether a road is closed.

The system (100) may also be used to discover turn restrictions. In one example, when the map is partitioned into paths, additional turn paths are inserted at each intersection to track traffic from each incoming direction to each outgoing direction. For example, at a four way stop, there are four incoming directions and four outgoing directions associated with each of the incoming directions: Right turn, Straight, Left turn, and U-turn. After a large number of GPS traces (135) have been processed, the traffic counters on these turn paths are examined. Those paths with no recorded traffic are automatically marked suspicious. Because there may be occasional law-breakers among the traffic fleet, the system (100) may continue to consider a turn path somewhat suspicious if its traffic count is non-zero but still very small. In some examples, rather than look at the raw traffic count, the count may be considered as a percentage of the traffic. Thus, the straight direction may represent, for example, 90% of the traffic flow, right-turns 9%, left-turns 0.0%, and U-turns 1.0%. In one example, the process may include Laplace "correction" in the computation, so that when there is very little data, the statistic tends to avoid 0%.

The system (100) may then compare each percentage to a pre-determined threshold near 0%, for example 0.1% or 0.01%. In one example this threshold may be dependent on the type of turn being analyzed. Those turn paths with smaller ratios may be automatically marked as suspicious. Where these are not yet marked in the map, the edit can be inserted into the map. In one example editor review may be requested by the system before the edits are inserted into the map. In another example, the percentage may instead be computed based on the outgoing link.

Sometimes GPS traces (135) may not be received by the system (100) for some external reason. In this case where data is not received, many roads will erroneously be deemed closed by their low traffic counts. In one example, the system (100) is not run when the system (100) has determined that the data is insufficient.

In an alternate example, a road may be considered closed based on its traffic count as compared to the incoming load at one of its end intersections. That is, the load that feeds this road from an intersection is considered as a percentage of all the incoming traffic to the intersection. In a symmetric way, the system (100) may consider the outgoing traffic load of the road that feeds an intersection as a percentage of all the outgoing traffic of the intersection. Alternately, the divisor may be represented as a weighted average of the incoming paths, according to the historical percentages that took each incoming turn. As a result, if there is little traffic in an area of a city for some any reason, the lower traffic experienced with the incoming traffic will be taken into account, and the outgoing traffic path will not be considered closed prematurely. Again, Laplace correction can be included so that when there are very few counts, the percentage tends away from 0%.

As briefly described above, the methods may be operated using GPS traces from only truckers, resulting in "closure" information that is advisory to other truck drivers only. That is, a road that no truckers ever take will be marked as such, so that when a truck driver uses a road so marked, they will get a notice that caution is advised, as it is not a normal route. Alternately, the trucker's GPS navigator could be restricted to strongly prefer roads that are typically used by other truckers during navigation. This style of operation could also be run for other specialized populations; e.g. snowmobiler drivers on backcountry trails, hikers on wilderness trails, etc. In order to determine the type of vehicle being associated with the GPS system running the system (100), the system (100) may receive data from a user of the GPS system indicative of the type of vehicle being driven. This information may cause the GPS system to direct one type of user along another route than would otherwise have been suggested by the GPS system.

The methods described above may be implemented using computer usable program code embodied on a computer readable medium. In one example, a computer program product for updating road maps on a GPS device may be used in which the computer program product comprises a computer readable storage medium comprising computer usable program code embodied therewith. In this example, the computer usable program code may comprise computer usable program code to, when executed by a processor, match a number of GPS traces received from a number of GPS trace sources with a digital map; computer usable program code to, when executed by a processor, process the number of GPS traces that are matched to a road in the digital map; computer usable program code to, when executed by a processor, process the number of GPS traces that are unmatched to any road in the digital map; computer usable program code to, when executed by a processor, receive a proposed changes to the road map based on the matched and unmatched GPS traces; and computer usable program code to, when executed by a processor, update roads and metadata associated with the roads based on the processed matched and unmatched GPS traces.

The specification and figures describe a system and method for updating road maps. The system and method comprises a matched segment module and unmatched segment that receives matched and unmatched GPS traces, respectively, and provides automatic updates to a digital map. The system (100) may be scaled up to include map data defining the entire earth's surface. The system (100) and method can further leverage large-scale GPS traces readily available from many location-tracking systems or services, e.g., fleet management systems, online navigation (implementing user locations to supply the relevant portion of the map), and live traffic services, and provide reciprocal benefits back to these systems. Additionally, the disclosed system and methods can be used for inferring personal or private roads for personalized maps, either for individuals or for private companies. Even further, the system and method may be used where only small volumes of data are available. Still further, the system and method may be used by a single vehicle to automatically correct over-restrictive turn restrictions in maps. In this limited mode, it could be used to correct personalized maps without requiring cooperation from a central system (100). The system and method also relieve a digital map source from having to hire a number of employees to update the ever increasing number of changes to the evolving road infrastructures in the world such as new roads, new intersections, changed turn restrictions at intersections, road closure and reopening, and changes to the allowable directional flow of traffic on a given road.

The preceding description has been presented to illustrate and describe examples of the principles described. This description is not intended to be exhaustive or to limit these principles to any precise form disclosed. Many modifications and variations are possible in light of the above teaching.

What is claimed is:

1. A system for updating road maps, comprising:
   a processor;
   a database, comprising data describing a number of roads;
   a map matching module configured to match a number of GPS traces with a number of roads;
   a matched segment module configured to process GPS traces that are matched to a subset of the number of roads;
   an unmatched segment module configured to process GPS traces that are unmatched with a road among the number of roads; and
   a map updating module configured to update a number of roads based on proposed changes presented by the matched segment module and the unmatched segment module;
   in which the map matching module is further configured to:
      partition the number of roads into a number of disjoint sections with the map matching module treating each of the number of roads as bi-directional;
      determine, based on a percentage of GPS traces in each direction along a disjoint section among the number of disjoint sections, the possible directional flow of traffic; and
      propose a change to the metadata in the database describing the allowable directional flow of traffic;
   in which, where it has been determined that a section within the number of sections is a one-way directional flow of traffic, the system is configured to imply one-way directional flow of traffic constraints on other sections within the number of sections.

2. The system of claim 1, in which the unmatched segment module is further configured to:
   cluster the unmatched GPS traces;
   select a cluster of unmatched GPS traces having at least a threshold number of GPS traces;
   produce a single road geometry for a cluster of unmatched GPS traces using a centerline fitting procedure, the single road geometry describing a new road not described in the database;
   determine a connection point for the single road geometry with an existing road within the database; and
   provide a proposed update to the map updating module.

3. The system of claim 1, in which the map updating module is further configured to notify a user of the system when the proposed change from the matched segment module, the unmatched segment module, or a combination thereof is produced and request confirmation from the user to update the database.

4. The system of claim 1, in which the map matching module is further configured to:
   receive a GPS trace that traverses a first and second road among the number of roads in which the first and second roads are not connected in the database and the traversal from the first to the second road indicates a divergence from the first road;
   in which the divergence is resolved by matching subsequent GPS points to the second road and ignoring the connectivity to the first road after a first distance threshold has been exceeded from a last known matched GPS point on the first road;
   determine that a discontinuity resulting from the divergence in the map matching process exists based on whether the first of the subsequent GPS points to the second road being matched with the second road is within a second threshold distance from the last known matched GPS point on the first road;
   create metadata describing a missing intersection; and
   provide a proposed update to the map updating module describing the missing intersection after at least a threshold number of discontinuities have been determined to exist.

5. The system of claim 4, in which the geometry of the missing intersection is determined by either:
   selecting the point of intersection of the first and second roads if the road geometries intersect within a threshold distance to the discontinuity; or
   selecting the point of intersection as being the closest point between the first and second road within a threshold distance to the discontinuity if the geometry defining the first and second roads does not intersect.

6. The system of claim 4, in which the map matching module is configured to observe metadata defining turn restrictions in the database and in which the metadata defining turn restrictions is updated after a threshold number of discontinuities are determined to exist in the metadata.

7. The system of claim 1, in which the partitioning the number of roads into a number of disjointed sections further comprises maintaining a number of road sections as joined together to form a single section where the intersections between the road sections provide no other path for traffic to travel.

8. The system of claim 1, in which the matched segment module is further configured to produce metadata associated with a road describing whether the road is closed for traffic by:
   partitioning each road into disjointed, single-direction paths with each path describing an allowed directional traffic flow for that road;
   setting each path to a training mode and receiving GPS traces describing travel along that path;

updating usage metadata associated with each path until a threshold number of GPS traces are received to determine usual traffic flow of any path; and providing a proposed update to the map updating module describing the metadata associated with a path as indicating the path as closed when the number of GPS traces within a period of time falls below a threshold.

9. The system of claim 8, in which the metadata associated with a road further describes roads that are closed to a type of vehicle based on:

whether, during the training mode, the GPS traces describing travel along that path indicates that a threshold number of GPS traces have not been received for that type of vehicle; and in which the road is marked closed to that type of vehicle when it is determined that the threshold is not met.

10. The system of claim 1, in which the matched segment module is further configured to produce metadata associated with a road describing turn restrictions at a traffic intersection by:

partitioning the number of roads into disjointed, single-direction sections with each section describing turn options available at the intersection of multiple sections;

setting each intersection to a training mode and receiving GPS traces describing travel through the intersection;

updating usage metadata associated with each intersection until a threshold number of GPS traces are received to determine usual traffic flow of any section;

proposing a change to the metadata to the map updating module describing turn restrictions at a traffic intersection based on the updated usage data; and providing a proposed update to the map updating module describing the metadata associated with a section as indicating the section is closed when the number of GPS traces within a period of time falls below a threshold.

11. A method of updating a road map on a GPS device comprising:

with a processor:

matching a number of GPS traces to a number of roads within a map database with a map matching module;

processing GPS traces that are matched to a subset of the number of roads with a matched segment module;

processing GPS traces that are unmatched with the roads with an unmatched segment module; and providing, at a map updating module, a proposed change based on processed GPS traces received from the matched and unmatched segment modules;

receiving a GPS trace that traverses a first and second road among the number of roads in which the first and second roads are not connected in the map database and the traversal from the first to the second road indicates a divergence from the first road;

in which the divergence is resolved by matching subsequent GPS points to the second road and ignoring the connectivity to the first road after a first distance threshold has been exceeded from a last known matched GPS point on the first road.

12. The method of claim 11, further comprising determining that the unmatched GPS traces form a new road not represented in the database by:

clustering the unmatched GPS traces;

selecting a cluster of unmatched GPS traces having a threshold number of GPS traces;

producing a single road geometry for a GPS trace cluster using a centerline fitting procedure, the single road geometry describing a new road not described in the database;

determining the connection point for the new road with an existing road within the database; and providing a proposed change describing the new road to the map updating module.

13. The method of claim 11, further comprising:

determining that a discontinuity resulting from the divergence in the map matching process exists based on whether the first of the subsequent GPS points to the second road being matched with the second road is within a second threshold distance from the last know matched GPS point in the first road;

creating metadata describing a missing intersection; and updating the database with the missing intersection after at least a threshold number of discontinuities have been determined to exist.

14. The method of claim 13, in which the geometry of the missing intersection is determined by either:

selecting the point of intersection of the first and second roads if the road geometries intersect within a threshold distance; or selecting the point of intersection as being the closest point between the first and second road within a threshold distance to the discontinuity if the geometry defining the first and second road do not intersect.

15. The method of claim 11, further comprising producing metadata associated with a road describing the directional flow of traffic on any of the roads by:

partitioning, with the map matching module, the number of roads into a number of disjoint sections with the map matching module treating each of the number of roads as bi-directional;

determining, based on a percentage of GPS traces in each direction along a disjoint section among the number of disjoint sections, the possible directional flow of traffic; and correcting the metadata describing the allowable directional flow of traffic when the number of sections is inconsistent with a description of the allowable directional flow of traffic on the road in the database.

16. The method of claim 11, further comprising producing metadata associated with a road describing whether the road is closed for traffic by;

partitioning each road into disjointed, single-direction path with each path describing an allowed directional traffic flow for that road;

setting each path to a training mode and receiving GPS traces describing travel along that path;

updating usage metadata associated with each path until a threshold number of GPS traces are received to determine usual traffic flow of any path; and updating the metadata associated with a path by marking the path as closed when the number of GPS traces within a period of time falls below a threshold based on the usual traffic flow associated with the path.

17. The method of claim 11, further comprising producing metadata associated with a road describing turn restrictions at a traffic intersection by;

partitioning the number of roads into disjointed, single-direction sections with each section describing turn options available at the intersection of multiple sections;

setting each intersection to a training mode and receiving GPS traces describing travel through the intersection;

updating usage metadata associated with each intersection until a threshold number of GPS traces are received to determine usual traffic flow of any section;

proposing a change to the metadata to the map updating module describing turn restrictions at a traffic intersection based on the updated usage data; and updating the metadata associated with a section by marking the section as closed when the number of GPS traces within a period of time falls below a threshold.

18. The method of claim 11, further comprising:

updating a version number of a road each time the data associated with the road is updated via the map updating module;

in which the version number of the road is taken into consideration when matching the number of GPS traces to the number of roads within a map database; and in which a version number indicating the road data is outdated prevents the map matching module from using the proposed change.

\* \* \* \* \*